United States Patent

Cassettari et al.

Patent Number: 5,295,745
Date of Patent: Mar. 22, 1994

[54] CALORIMETER FOR TIME/TEMPERATURE MEASUREMENTS OF THERMOSETTING RESINS (THERMOSETS)

[75] Inventors: Mario Cassettari, Pisa; Fabio Papucci, Cascina; Giuseppe Salvetti, San Giuliano Terme; Elpidio Tombari, Pietrasanta; Stefano Veronesi, Calci, all of Italy

[73] Assignee: Consiglio Nazionale Delle Richerche, Rome, Italy

[21] Appl. No.: 942,575

[22] Filed: Sep. 9, 1992

[30] Foreign Application Priority Data

Sep. 13, 1991 [IT] Italy ............... FI/91/A-226

[51] Int. Cl.$^5$ ............... G01N 25/20; G01K 17/00
[52] U.S. Cl. ............................ 374/010; 374/33
[58] Field of Search ............... 374/10, 11, 12, 13, 374/208, 31, 32, 33, 36

[56] References Cited

U.S. PATENT DOCUMENTS

| | | | |
|---|---|---|---|
| 3,285,053 | 11/1966 | Mazieres | 374/13 |
| 3,314,288 | 4/1967 | Sherwin | 374/13 |
| 3,379,061 | 4/1968 | Mercier | 374/33 |
| 3,417,604 | 12/1968 | Bean et al. | 374/11 |
| 3,899,918 | 8/1975 | Privalov et al. | 374/11 |
| 4,368,991 | 1/1983 | Hentze | 374/12 |
| 4,567,849 | 2/1986 | Wan | 374/11 |
| 4,859,077 | 8/1989 | Ito et al. | 374/31 |

FOREIGN PATENT DOCUMENTS

| | | |
|---|---|---|
| 9528 A/86 | 11/1986 | Italy . |
| 9471 A/90 | 8/1990 | Italy . |

OTHER PUBLICATIONS

*Science* 131 (3401) pp. 661-662. Mar. 4, 1960, Q1 534, "Differential Thermal Study of Pyrosynthesis".
*CERN European Organization for Nuclear Research* vol. 77, No. 3, Feb. 7, 1977, Geneva, pp. 15, 62, 42, 58. M. Van De Voorde, "Low Temperature Irradiation Effects on Materials and Components for Superconducting Magnets for High-Energy Physics Applications".
*Review of Scientific Instruments* vol. 60, No. 7.1, Jul. 1979, XP38264, A Barbini et al. "Differential Microcalorimeter for Liquid Samples".

*Primary Examiner*—William A. Cuchlinski, Jr.
*Assistant Examiner*—G. Bradley Bennett
*Attorney, Agent, or Firm*—McGlew and Tuttle

[57] ABSTRACT

The calorimeter comprises an external accommodating head (23) with two cavities (26, 27) which are capable of receiving a measurement cell (29), in which the specimen to be examined is inserted, and a reference cell (31); the cells (29, 31) are surrounded by a thermoresistor (229), the variation of the resistance of which is determined by a temperature variation, and a heater (129). The two cavities (26, 27) are closed by covers (35, 37) traversed by tubular stems (47-49) capable of supporting the cells (29, 31) for the insertion, into one of them, of a specimen contained in a tubular container (53), which is immersed in a chamber (29A) in which a fluid having high thermal conductivity is present; said cavities (26, 27) are reached by conduits (41, 43; 45) so as to be subjected to vacuum or to controlled pressure using replaceable gases (air, hydrogen, etc.).

4 Claims, 1 Drawing Sheet

Fig.1
Fig.2
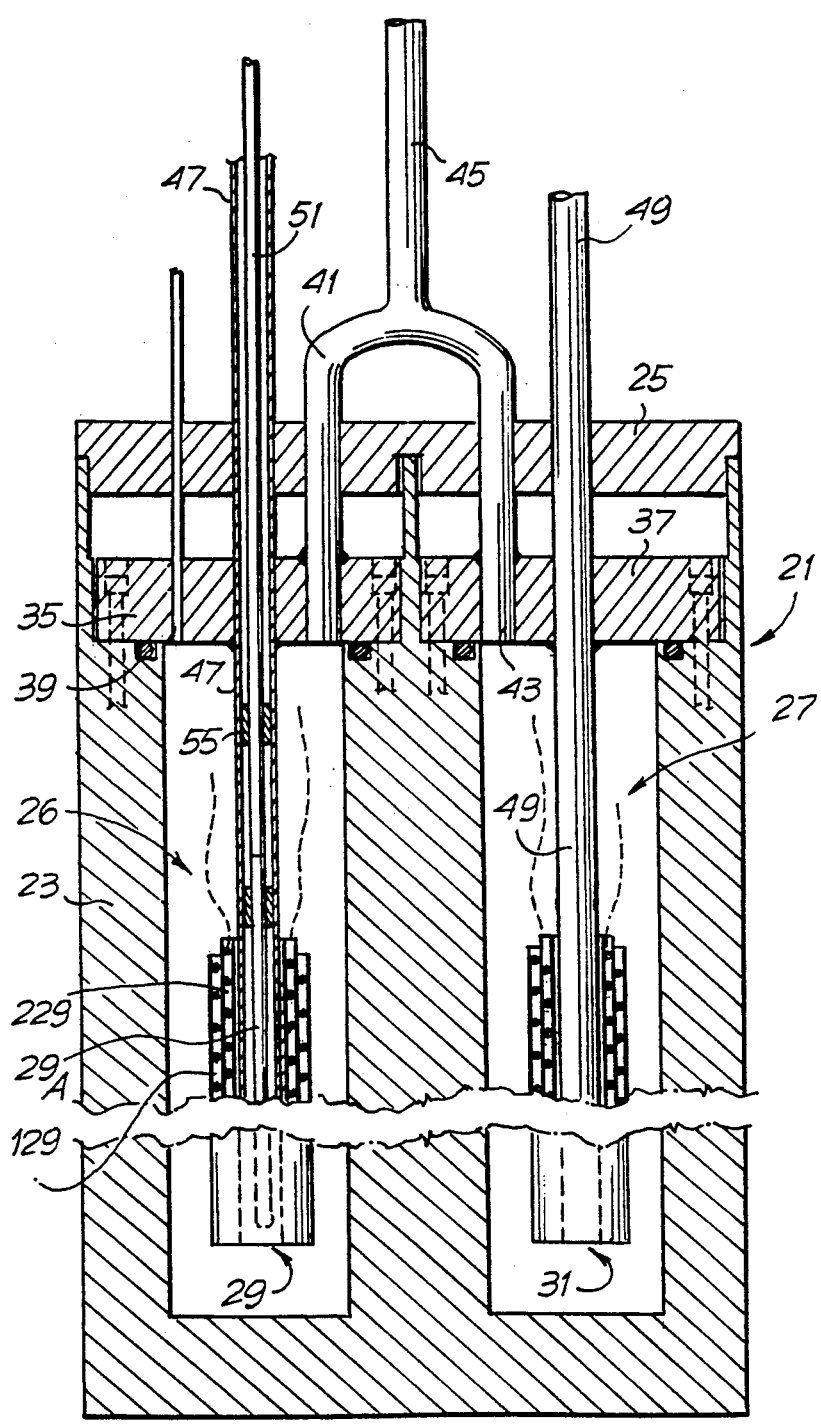
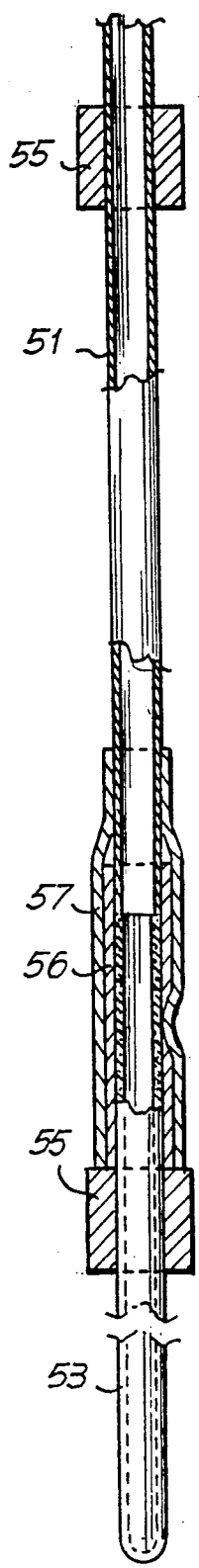

CALORIMETER FOR TIME/TEMPERATURE MEASUREMENTS OF THERMOSETTING RESINS (THERMOSETS)

FIELD AND BACKGROUND OF THE INVENTION

The invention relates to a calorimetric cell capable of taking measurements as a function of the time and of the temperature of thermosetting resins referred to as thermosets. This cell is derived from the calorimeters according to IT Patents No. 1,216,296 on application No. 9528 A/86 and also according to application No. 9471 A/90 of the same proprietor organization, to which patents reference is made. In particular, there is no change in the principle of operation using a sensor and heater which are uniformly wound on a long cylindrical metal tube, and using phase detection of the signal generated by the variation in temperature of the cell containing the specimen with respect to the reference cell, by means of the measurement of the imbalance of a Wheatstone resistance bridge.

SUMMARY OF THE INVENTION

The calorimeter concerned is of the type comprising an external accommodating head with two cavities which are capable of receiving a measurement cell, in which the specimen to be examined is inserted, and a reference cell; each of the two cells comprises a cylindrical element on which there is uniformly distributed a thermoresistor having a high temperature coefficient, which is connected to means which are capable of measuring the variation in resistance thereof determined by a temperature variation, and a heater. According to the invention, the two cavities are closed by covers traversed by tubular stems capable of supporting the cells and of permitting the insertion, into one of them, of a specimen contained in a tubular container, which is immersed in a chamber in which a fluid having high thermal conductivity is present; said cavities are reached by conduits so as to be subjected to vacuum or to controlled pressure using replaceable gases (air, hydrogen etc.).

In practice, the container can be engaged at the end of a handling and suction tube which can be guided within said tubular stem supporting the measurement cell.

Said container can be welded at the end after suction of the specimen via said tube.

The calorimeter further comprises means for carrying out measurements, sequenced in time, of the temperature of the specimen during its exothermic reactions, and of that of the reference.

The invention will be more clearly understood by following the description and the accompanying drawings, which shows a non-limiting practical illustrative embodiment of said invention.

In the drawings:

FIG. 1 shows a cross section by way of demonstration; and

FIG. 2 shows, in particular, the tubular stem.

DETAILED DESCRIPTION OF THE PREFERRED EMBODIMENTS

In the drawing (FIG. 1) of the measurement head 21, 23 indicates an external housing equipped with a closing cover 25. Within the housing 23 two cavities 26, 27 for the respective cells 29 and 31 are formed. Each cavity 26, 27 is closed by means of two sealed closing covers 35, 37 with annular gaskets 39 (of the O-ring type). Within each cavity 26, 27 it is possible to maintain a controlled pressure, from a few bars down to a vacuum ($1\mu$ bar), using various gases to modify the heat exchange coefficient; for this purpose, there are provided tubes 41, 43 connected to one another to form a conduit 45.

Within the covers 35 and 37 are engaged tubular stems 47 and 49, open at the top, terminating—at their lower end inside the cavities 26 and 27—with the respective cells 29 and 31 which are virtually identical. The measurement cell 29 is essentially formed by a chamber 29A surrounded by the heater 129 and by the detector 229. In particular, the cell 29 exhibits the cylindrical element 47, produced with a stainless steel tube, on which there is provided a layer of insulator to receive, in wound form, a filament of the sensor 229 of spiral shape, produced in an alloy having a high temperature coefficient, for example Hytemco, alloy 99, etc. Thus, the filament 229 constitutes a thermoresistor, the resistance of which is greatly dependent upon the temperature and accordingly constitutes a temperature sensor. The insulator, which may be constituted by a thin strip of "Teflon", serves to prevent the slipping of the filament both during the winding thereof and during the thermal cycles to which the instrument is subjected. As described in the above cited patent documents, the thermoresistors of the two cells 29 and 31 are inserted in a Wheatstone bridge, the imbalance of which constitutes a voltage signal which is employed for the detection of one or more thermodynamic characteristics of the specimen. Around the thermoresistor 229 there is disposed an insulating layer, and on the latter is wound the heating resistor 129, which is capable of supplying heat in a controlled manner to the cell, for all those measurements requiring a controlled supply of heat energy to the specimen. The thermoresistor and the heating resistor will be connected in a suitable manner to connectors for the external connections.

FIG. 2 illustrates, in particular, a component which can be inserted in the tubular stems 47 and 49 for the measurements indicated below. This component comprises a long tube 51 with thin walls of stainless steel and a tubular container 53 of "Pyrex" glass with thin walls which is capable of containing the specimen of thermoset. 55 indicates small centering cylinders of aluminum (or the like). The container 53 is in part surrounded by a rigid sheath 56 fixed to the tube 51 which is, in its turn, surrounded by a tubular sheath of silicone 57; through a lateral aperture of the sheath 56, the silicone 57 is capable of supporting the container 53.

In practice, the container 53 is open at the bottom, so that it is possible to aspirate the resin into the latter; the container is then heat-sealed.

With the described arrangement, it is possible to introduce into the specimen cell 29 the cylindrical container 53 of pyrex glass with thin walls, which has previously been weighed and then filled with the thermoset. The is thermally coupled—by means of a liquid interposed in the interspace formed by the walls of the chamber 29A and by the surface of the container 53—with the sensor and the heater 229 and 129.

It is then possible to carry out simultaneous and automatic measurements, over a period of time, both of the quantity of heat released during the hardening process (polymerization enthalpy) and of the variation in thermal capacity of the specimen. The variation of enthalpy H of the specimen is obtained using the relation:

$$\frac{dH}{dt} = [C_o + C_c(t)]\frac{d}{dt}[T_c(t) - T_r] + \lambda[T_c(t) - T_r]$$

where Co is the thermal capacity of the cell without a specimen and Cc(t) is the thermal capacity of the specimen at the time t, λ is the coefficient of heat exchange between the specimen cell and the external environment and [Tc(t)-Tr] is the temperature difference between the specimen cell T(c) and the reference cell Tr. The value [Tc(t)-Tr] is the physical quantity directly measured. The individual values of the thermal capacity Co and Cc(t) are measured, during the process of hardening of the thermoset, by means of the same procedure which has been described in the two above cited patent documents.

It is possible, when the process has been completed, to extract the container 53 of the thermoset and to determine the mass m of said thermoset by difference in weighings. Knowing m, dH/dt and Cc(t), it is possible to characterize the material quantitatively, from a calorimetric point of view, during the hardening process.

Still with the described arrangement, it is possible to carry out the measurement of dH/dt and Cc(t) at time intervals which may be reduced to approximately 200 sec. by virtue of the introduction, into the cavities 26 and 27, of $H_2$ at a pressure of approximately 1 bar, via the conduits 45, 41 and 43. In this way, an increase is achieved in the coefficient of heat exchange λ of the cells 29, 31 of approximately four times as compared with the heat exchange which is possible in air. Alternatively, in the case where the process is very slow, it is possible to achieve a forced vacuum in such a manner as to obtain quasi adiabatic conditions (λ very small). It is then possible to undertake processes which take place both on relatively fast time scales (less than one hour) and very slowly (of the order of days).

The measurement technique which can be achieved using the instrument permits the monitoring of the development, with time, of the specific heat of a specimen subjected to a reaction which is per se highly exothermic; it is precisely the considerable quantity of heat developed during the process, which does not permit the measurement of the specific heat by means of conventional calorimeters.

The possibility—now achieved—of measuring the specific heat of thermosetting resins and of polymers in general during the process of formation permits the individualization of the phase transitions which take place, and thus the tracing of the mechanical and structural properties of said specimen.

The deepening of knowledge which derives from these measurements as to the kinetics of hardening and the processes of ageing of thermosets are of great importance in the optimization of the quality of materials and of the production and working techniques, and of great practical interest, considering also the widespread use of these materials.

It is understood that the drawing shows only an illustrative embodiment which is given only by way of practical demonstration of the invention, it being possible for this invention to vary in terms of form and arrangement without thereby departing from the scope of the concept which forms the basis of said invention.

We claim:

1. A differential calorimeter, comprising:
    an external accommodating head defining two cavities;
    a measurement cell in which an inserted specimen may be examined;
    a reference cell, each of said measurement cell and said reference cell including a cylindrical element with a uniformly distributed thermoresistor uniformly distributed thereon, said thermoresistor having a high temperature coefficient and being connected to measurement means for measuring a variation in resistance of said thermoresistor wherein variations in resistance correspond to temperature variations;
    tubular stems, one of said tubular stems being connected to said measurement cell and one of said tubular stems being connected to said reference cell for support of said measurement cell and said reference cell respectively;
    a tubular container for holding the specimen, one of said tubular stems defining a chamber wherein said tubular container may be inserted therein, said chamber having a fluid with high thermal conductivity present therein;
    conduit means for controlling pressure in said two cavities;
    covers closing said two cavities, said covers including openings for said tubular stems.

2. The calorimeter according to claim 1, wherein said tubular container is connected to an end of a handling and suction tube, said handling and suction tube being guidable within one of said tubular stems supporting said measurement cell.

3. The calorimeter according to claim 2, wherein said tubular container includes a weldable end for closing said tubular container after suction of said specimen via said suction tube.

4. The calorimeter according to claim 1, wherein said measurement means includes means for carrying out measurements, sequenced in time, of the temperature of the specimen whereby said measurements may be carried out during an exothermic reaction of said specimen.

* * * * *